(12) United States Patent
Metzner

(10) Patent No.: US 6,821,432 B2
(45) Date of Patent: Nov. 23, 2004

(54) MEASURING APPARATUS AND A MEASURING METHOD FOR THE DETERMINATION OF PARAMETERS OF MEDICAL FLUIDS

(75) Inventor: Klaus Metzner, Friedrichsdorf (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 145 days.

(21) Appl. No.: 10/230,227

(22) Filed: Aug. 29, 2002

(65) Prior Publication Data

US 2003/0042181 A1 Mar. 6, 2003

(30) Foreign Application Priority Data

Sep. 3, 2001 (DE) .......................................... 101 43 137

(51) Int. Cl.[7] .............................................. B01D 61/32
(52) U.S. Cl. ............................ 210/646; 33/706; 33/708; 73/1.79; 73/866.1; 73/866.5; 210/85; 210/96.2
(58) Field of Search ........................... 210/85, 94, 96.1, 210/96.2, 645, 646, 739, 745; 33/706, 708; 73/1.02, 1.16, 1.37, 1.79, 866.1, 866.5; 356/3, 39, 300, 317; 422/68.01, 82.05, 82.08, 82.09, 68.1; 436/8, 68, 164, 165, 172

(56) References Cited

U.S. PATENT DOCUMENTS

| | | | |
|---|---|---|---|
| 4,370,983 A | * | 2/1983 | Lichtenstein ................ 600/301 |
| 4,508,622 A | * | 4/1985 | Polaschegg et al. ........ 210/96.2 |
| 5,770,454 A | * | 6/1998 | Essenpreis et al. .......... 436/164 |
| 6,037,178 A | * | 3/2000 | Leiner et al. .................. 436/50 |
| 6,101,406 A | | 8/2000 | Hacker et al. |

FOREIGN PATENT DOCUMENTS

| | | |
|---|---|---|
| AU | 407 303 | 6/2000 |
| DE | 19605652 | 8/1997 |
| DE | 197 46 199 | 4/1999 |
| DE | 198 37 667 | 3/2000 |

\* cited by examiner

*Primary Examiner*—Joseph Drodge
(74) *Attorney, Agent, or Firm*—Jacobson Holman PLLC

(57) ABSTRACT

A measuring apparatus for the determination of parameters of medical fluids with a measured region which including a measuring chamber device for receiving a disposable cassette with at least one measuring chamber through which the fluid to be measured is guided, and at least one measuring element for measuring a measured value whose value depends on the extent of the measuring chamber in a measuring direction and allows the determination of the parameter, or of a value being in a fixed relationship thereto, with a known extent of the measuring chamber. A distance sensor unit is provided which is arranged relative to the measuring chamber such that the measured distance changes relative to the extent of the measuring chamber. A method is also provided for the determination of parameters of medical fluids which can be carried out with the measuring apparatus, and for the calibration of the measuring apparatus.

19 Claims, 2 Drawing Sheets

MEASURING APPARATUS AND A MEASURING METHOD FOR THE DETERMINATION OF PARAMETERS OF MEDICAL FLUIDS

BACKGROUND OF THE INVENTION

1. Field of the Invention

The invention relates to a measuring apparatus for the determination of parameters of medical fluids, the apparatus having a measuring chamber device for receiving a disposable cassette with at least one measuring chamber through which the fluid to be measured is guided, and at least one measuring element for measuring a measured value whose value depends on the extent of the measuring chamber and allows for determination of the parameter, or of a value being in a fixed relationship thereto, with a known value for the extent of the measuring chamber. The present invention also relates to a method for the determination of medical fluids by leading the fluid through a measuring chamber, and measuring a measured value whose value depends on the extent of the measuring chamber in a measuring direction, the measured value allowing for determination of the parameter, or of a value being in a fixed relationship thereto, with a known value for the extent of the measuring chamber. Further included in the present invention is a method for the calibration of a measuring apparatus for the determination of parameters of medical fluids.

2. Description of the Related Art

It is, for example, helpful in dialysis treatment for the blood temperature, the blood volume and/or the air portion to be determined in the extra-corporeal blood circulation during the treatment.

For this purpose, for example, the blood is led during the dialysis treatment in the extra-corporeal blood circulation through a disposable cassette such as is described in DE 198 37 667 A1. Such a disposable cassette consists of a plastic part which, in turn, consists of two further parts. Passages and volumes are let into a hard part. This hard part is closed by a flexible film for the covering of the channels and volumes. The disposable cassette is introduced into a special receiving chamber, e.g. on a dialyser.

This chamber can, for example, be opened with the help of a pivotable door. The disposable cassette is inserted into the chamber, with the flexible film lying opposite a corresponding opposing piece on the machine such that the cassette can be operated with the aid of actuators and sensors on the machine side. The door is closed and thereby serves as an abutment. Sensors, e.g. a temperature sensor or a pressure sensor, can be provided in the chamber for the determination of various parameters of the blood during the dialysis treatment.

Furthermore, a light barrier can be provided to determine whether blood is flowing through the passages. A run time measurement can be carried out through a measuring chamber in the disposable cassette with the aid of an ultrasonic measuring unit, which allows a determination of the blood density, of the concentration and/or of the haematocrit value.

To be able to determine the desired parameters precisely from the run time, the ultrasonic path must be known as accurately as possible. With the known solution of DE 198 37 667 A1, the disposable cassette is for this reason held in the receiving chamber with the aid of spacer bolts and screw connections such that a precise spacing results.

Such a design is, however, complex and requires a fairly long preparation of the dialysis treatment. The arrangement is sensitive to contamination and wear due to the spacer bolts. The pressing forces which act on the cassette during a treatment, which can take several hours, can result, for example, in a plastic deformation of the cassette and thus of the spacing. On the other hand, openings through the cassette and the film are required to be able to fix the spacer bolts in place.

SUMMARY OF THE INVENTION

Starting from this prior art, it is the object of the present invention to provide an apparatus and a method with which the accurate determination of a parameter of a medical fluid is possible whose value is dependent on the extent of a measuring chamber, wherein the apparatus should be insensitive to wear and contamination and the handling of the apparatus and of the measuring process should be easy.

This object, as well as others, is solved by a measuring apparatus and a measuring method according to the present invention. A calibration process in accordance with the present invention for a measuring apparatus in accordance with the invention is also provided.

With the measuring apparatus in accordance with the invention, at least one distance sensor unit is provided which is arranged relative to the measuring chamber such that the distance measured changes relative to the extent of the measuring chamber. With such a distance sensor unit, a distance can be determined, which depends on the extent of the measuring chamber, during the measurement of a measured value which depends on the extent of the measuring chamber. The measured value allows the determination of the medical parameter in question when the extent of the measuring chamber in the measuring direction is known. It is therefore possible with the apparatus in accordance with the invention to determine not only the measured value dependent on the distance during the treatment, but also the distance, or its change, itself. The desired parameter can thus be directly determined from these values and e.g. represented and monitored on a corresponding display unit. Naturally, both the parameter determined in this manner and other values in a fixed relationship with it can be used directly for the control of the treatment, e.g. for a change of the temperature, the flow rate or other parameters relevant during dialysis treatment.

At the start of the treatment, e.g. of a dialysis treatment, only the disposable cassette has to be connected and closed. No particular care must be taken to precisely adjust the distance of the two elements of the receiving chamber for the disposable cassette, since the signal of the distance sensor unit is taken up during the treatment and the extent of the measuring chamber in the measuring direction of the measuring element can be accurately determined.

Tolerance fluctuations of the disposable receiver during the treatment, e.g. due to different fluid pressure values or temperature changes, are automatically taken into account and do not require any special correction.

The distance sensor unit can here be disposed directly in the region of the measuring chamber. The extent of the measuring chamber in the measuring direction can be determined directly in this manner without the measured distance signal having to be additionally converted into the extent of the measuring chamber. In other arrangements, it can be advantageous for the distance sensor unit to be located offset with respect to the measuring chamber. The distance between the two elements can likewise be determined, but the measurement of the fluid sent through the measuring apparatus remains unaffected.

With an advantageous embodiment, the distance sensor unit comprises two parts which do not contact one another and which are arranged relative to the measuring chamber such that their relative distance changes with the extent of the measuring chamber.

The distance sensor unit can be e.g. a capacitive unit, with the two parts comprising the electrodes of a capacitor. A change in the distance of the capacitor plates changes the capacity, which can be determined in a known manner. An optical distance measurement can likewise be provided.

With a particularly advantageous embodiment, the distance sensor unit comprises at least one unit for the generation of an electrical and/or magnetic field and at least one field sensor for the measurement of the field or its change. If the distance between the field generation device and the field sensor changes, then the field also changes, e.g. in its strength and/or direction. A conclusion can be made on the distance change from this field change. With a suitable calibration, the distance can also be determined absolutely.

If a magnetic field is used for the distance measurement, the change of the distance can be determined e.g. by induced eddy currents.

However, the magnetic field measurement is particularly simple to realise with the aid of a magneto-resistive sensor such as is described in DE 197 46 199. With such a magneto-resistive sensor, the resistance of a sensor arrangement changes in an easily measurable manner when the magnetic field passing through it changes. If now an element generating a magnetic field, for simplicity's sake e.g. a permanent magnet, is located e.g. on one side of the disposable cassette, and if a magneto-resistive sensor is located on the other side of the disposable cassette, then the signal of the magneto-resistive sensor is dependent on the distance which is in turn directly related to the extent of the measuring chamber. The electrical signal of the magneto-resistive sensor can be measured easily and evaluated precisely. With a sensor in accordance with DE 197 46 199, the direction of the magnetic field with respect to the sensor axis is detected with the help of a sensor. The arrangement in accordance with the invention is then selected such that the direction of the magnetic field at the location of the field sensor is unambiguously related to the distance of the field sensor from the field generation device in order to thus determine the distance from the direction of the magnetic field.

With the dialysis treatment, the accurate knowledge of the water content and/or of the blood density related to this is necessary. The density measurement can comprise e.g. a light absorption measurement. However, the measurement of the run time of an ultrasonic wave through the blood, with the sound velocity being dependent on the density, is particularly accurate. A conclusion can thus also be drawn on the haemocrit value from the run time. For the ultrasonic measurement, an ultrasonic sensor can be provided on one side of the measuring chamber and an ultrasonic receiver on the opposite side of the measuring chamber. Naturally, the sensor and the receiver can also be provided on one side of the measuring chamber and only an ultrasonic reflector on the other side.

With such a design of the measuring apparatus, the run-time of the ultrasonic wave can be defined as the measured value. The desired medical parameter can be determined from this measured value with a known distance of the ultrasonic measuring elements, with the determination of this distance or its change being accurately possible with the measuring apparatus in accordance with the invention. Naturally, the ultrasonic speed can also be itself determined in this manner.

The distance can be monitored at a point of the disposable cassette with the help of a distance sensor unit and thus a conclusion can be drawn on a change of the extent of the measuring chamber in the measuring direction. A higher accuracy can be achieved if distance sensor units are provided at a plurality of points of the measuring apparatus offset with respect to one another. In this manner, a tilting or displacement of the different parts of the measuring apparatus can also be detected.

With a method in accordance with the invention for the determination of parameters of medical fluids, a value being in a fixed relationship to the extent of the measuring chamber in the measuring direction or to the change in the extent is determined during the determination of a measured value whose value depends on the extent of a measuring chamber. With the method in accordance with the invention, a magnetic field is particularly advantageously determined for the determination of the distance of a field sensor and of a field generation device in order to be able to determine the extent of the measuring chamber from this distance. As described, a direction determination of the magnetic field can e.g. be used for this purpose when the direction of the magnetic field at the location of the field sensor depends on the distance of the field sensor from the field generation device.

An accurate monitoring of the extent of a measuring chamber, e.g. in a disposable cassette, during the dialysis treatment is possible with the measuring apparatus in accordance with the invention and with the measuring method in accordance with the invention. Parameters which are determined from a measured value which is dependent on the extent of the measuring chamber can thus be determined accurately and simply. The measuring apparatus is insensitive to contamination and wear and can be easily operated. A particularly accurate adjustment or separate monitoring of the distance is not necessary.

BRIEF DESCRIPTION OF THE DRAWINGS

The measuring apparatus in accordance with the invention and the measuring method in accordance with the invention will be explained in detail with respect to the enclosed Figures which represent preferred aspects. In this connection, there are shown FIG. 1 a side sectional view of an embodiment of a measuring apparatus in accordance with the invention with an inserted disposable cassette.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modification within the spirit and scope of the invention will become apparent to those skilled in the art from this detailed description.

Figure 1:
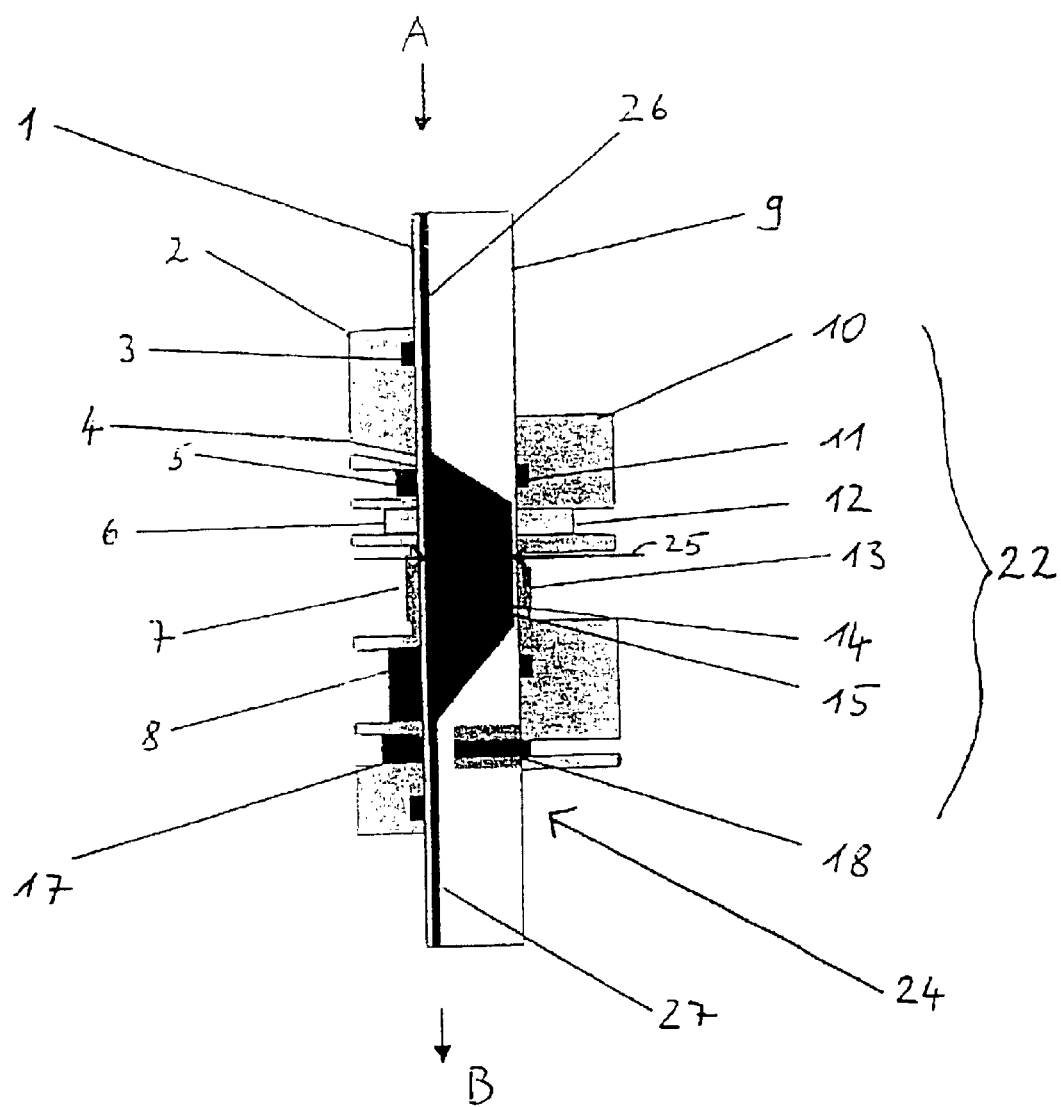

FIG. 1 shows the measuring apparatus in accordance with the invention with an inserted disposable cassette 9. The disposable cassette is inserted in a receiving chamber of e.g.

a dialyser. A measuring chamber 15 is integrated in the disposable cassette 9 and has an inflow 26 and an outflow 27 and a depth 25. The measuring chamber 15 is closed by a film 1, 14 on respectively opposite sides. Sensor carriers 2, 10, which each have a seal 3, 11 on their outer edge, contact the films 1, 14 at either side of the measuring chamber. In this connection, the seal is inserted into a groove respectively provided for this purpose and projects slightly beyond the lower side of the sensor carrier. In this connection, FIG. 1 shows the measuring region 22 of the disposable cassette for use in a dialysis treatment. The sensor carriers are part of the dialyser.

A temperature sensor 5 allows the measurement of the temperature of blood in the measuring chamber 15. Receivers 6 and transmitter 12 of a light barrier determine whether blood is flowing through the measuring chamber. A pressure sensor 8 contacts the film 1 which closes the measuring chamber 15 such that the pressure of the blood can be determined. A measuring element 7, 13, in the case shown being an ultrasonic receiver 7 and an ultrasonic transmitter 13, are located at either side of the measuring chamber with a connection 4 for underpressure. A distance sensor unit 24 consisting of two parts 17 and 18 and the individual sensors 5, 6, 12, 7, 13, 7, 24 are connected in a manner not shown to display units or to control unit, e.g. a microprocessor.

A and B designate the flow direction of the blood through the disposable cassette during the dialysis treatment.

Figure 2:
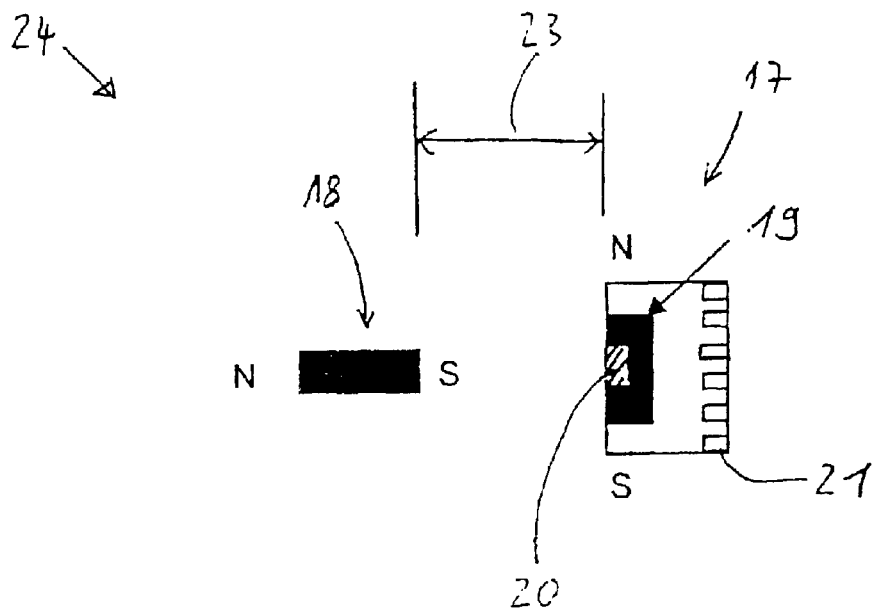
FIG. 2 schematically, a detail of FIG. 1.

FIG. 2 shows the distance sensor unit 24 schematically enlarged in detail. A first magnet 18 with the exemplary arrangement of the north pole and the south pole is disposed in the sensor carrier 2. The second part 17 of the distance sensor unit 24 is disposed in the other sensor carrier 10 on the other side of the cassette. This part comprises a second magnet 19 and a magneto-resistive sensor 20. Connectors 21 are indicated schematically. The poles, north pole and south pole, of the second magnet 19 are again only indicated by way of example. The distance, which is to be monitored, between the two parts 17 and 18 of the distance sensor unit 24 is designated by 23. With the arrangement of FIG. 2, a magnetic field is generated at the position of the sensor 20 by the magnet 18, with the field lines of said magnetic field extending practically horizontally, in the example shown from right to left. The magnetic field of the second magnet 19, in contrast, results in a magnetic field at the location of the sensor with a dominant vertical component (here from the bottom to the top). The resulting magnetic field has an alignment in the drawing plane differing in dependence on the distance 23 of the two magnets 18, 19. If the distance 23 is large, then the magnetic field corresponds rather to the second magnet 19. If the distance is small, then with the arrangement shown, the field vector tilts to the left since a horizontal component is mixed into the field vector. So that an appreciable rotation results, it is meaningful—depending on the arrangement relative to the sensor—to arrange the two magnets rotated with respect to one another as in FIG. 2. With such an arrangement, the field angle relative to a sensor axis, and thus the direction of the magnetic field with which the distance is directly correlated, can be measured.

Figure 3:
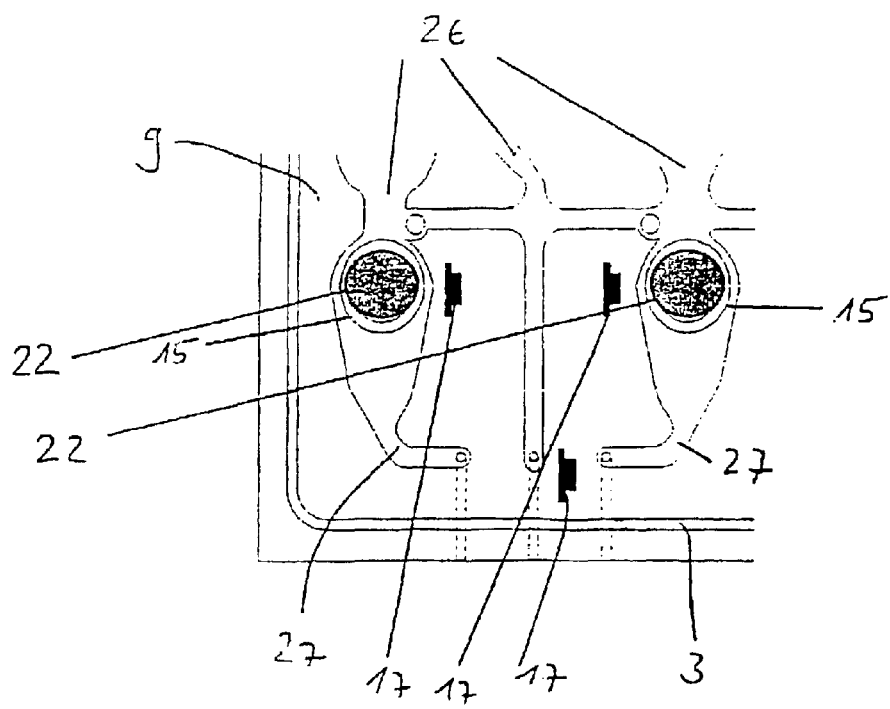
FIG. 3 a sectional view of a disposable cassette with indicated measuring devices.

In FIG. 3, a disposable cassette is shown in section. The disposable cassette 9 is visible with the passages 26 let into it for the inflow and the passages 27 for the outflow of the blood. In FIG. 3, the disposable cassette is shown together with the imagined position of the sensor parts 17 of the distance sensor unit 24 disposed behind it which are located behind the disposable cassette 9 when the cassette is inserted into the dialyser. Furthermore, with the example shown, two measured regions 22 are shown schematically. If the disposable cassette 9 is inserted into the corresponding receiving chamber of the dialyser, then the sensors such as the optical sensor 6, 12, the temperature sensor 5 or the pressure sensor 8 are disposed in these regions, as shown in FIG. 1. Furthermore, the measured regions 22 have e.g. the ultrasonic run time measuring sensor 7, 13.

The measuring device is preferably used for dialysis treatment. For this purpose, the measuring device is switched into the extra-corporeal blood circulation after insertion of the disposable cassette. The blood flows in the direction of the arrows A, B.

Before the individual measurements, underpressure is first applied to the films, e.g. via the connector 4 or comparable connectors, such that the films 1, 14 are in good contact with the sensors. The sensors can be controlled via a control unit, not shown in more detail, such that the respective measurements can begin.

For the measurement of the blood density, or of the haemocrit value, an ultrasonic wave is sent through the measuring chamber 15 with the aid of the ultrasonic transmitter 13 and is received by the ultrasonic receiver 7. The measured parameter measured in this connection is the run time of the ultrasonic wave which depends on the sound velocity, which is in turn dependent on the haemocrit value or on the density of the blood. With the aid of the distance sensor unit 24, the distance is determined between the parts 17, 18 of the distance sensor unit by reading the magneto-resistive sensor 20. This distance is connected in a fixed relationship with the distance of the sensor carrier 2, 10 and allows in this manner the exact determination of the distance of the ultrasonic transmitter 13 and of the ultrasonic receiver 7. The desired parameter (e.g. the sound velocity and thus the composition of the blood) can be determined with the aid of the measured run time and the distance determined in this manner which corresponds to the extent or depth 25 of the measuring chamber 15 and can then, optionally, be monitored and, optionally, used to control the treatment.

An exact adjustment of the individual sensor carriers 2, 10 is not necessary due to the precise distance determination, or its change, with the aid of the distance sensor unit 24. With an embodiment in accordance with FIG. 3, a tilting or displacement can also be determined from the different signals of the individual distance sensor units displaced with respect to one another.

The magneto-resistive distance sensor can be calibrated as follows. The ultrasonic measuring device 7, 13 can be used in this connection. On the construction of the dialyser, the ultrasound run time t1, which the sound takes from the ultrasonic sensor parts 7, 13 to the liquid, is determined ex works with the help of a disposable cassette of known properties and a fluid of known properties, such as a saline solution. This time t1 comprises, on the one hand, the time which the sound takes from the transmitter 13 up to the disposable cassette 9 and from the disposable cassette 9 up to the receiver 7. On the other hand, that time is considered in this sound run time t1 which the sound moves in those parts of the disposable cassette 9 which are arranged between the sensors 7, 13. With the embodiment shown in FIG. 1, these are e.g. the films 1 and 14.

Before a treatment, a known fluid, e.g. a saline solution, in turn flows through the disposable cassette 9 for calibration. The temperature sensor 5 can be used for the temperature correction of the sound run time. The total run time t of the ultrasound from the transmitter 13 to the receiver 7 is measured with the disposable cassette inserted. Said time consists of the known time t1 and the run time t2, which corresponds to the sound path in the saline solution in the measuring chamber 15. In this manner, t2 can be determined from the measured run time t and the known sound run time t1. The temperature dependent propagation speed in the saline solution is known, whereby the distance 25, which corresponds to the measuring path within the fluid, can be determined. Subsequently, the distance between the sensor plates 2, 10 is enlarged or reduced a little. This can be done, for example, using an apparatus of no further interest here with which one of the sensor plates can be moved.

In this connection, the calculated distance and the measuring signal of the magnetoresistive sensor are respectively recorded and stored. A characteristic curve is thus obtained which, with the help of the magneto-resistive sensor, allows a distance measurement with an unknown fluid. Such a calibration allows the detection of distance changes in an order of magnitude of 1 $\mu$m.

The invention being thus described, it will be apparent that the same way may be varied in many ways. Such variations are not to be regarded as a departure from the spirit and scope of the invention, and all such modifications as would be recognized by one skilled in the art are intended to be included within the scope of the following claims.

What is claimed is:

1. A measuring apparatus for the determination of a parameter of a medical fluid with a measured region which comprises the following:
    a measuring chamber device for receiving a disposable cassette with at least one measuring chamber through which the fluid to be measured is guided;
    at least one measuring element for measuring a measured value whose value depends on an extent of the measuring chamber and allows for determination of the parameter, or of a value being in a fixed relationship thereto, with a known value for said extent of the measuring chamber, and
    at least one distance sensor unit which is arranged relative to the measuring chamber device such that a distance measured by said distance sensor unit changes relative to the extent of the measuring chamber.

2. A measuring apparatus in accordance with claim 1, wherein the at least one distance sensor unit includes at least two parts which do not contact one another and which are arranged relative to the measuring chamber device such that a distance between said two parts changes with the extent of the measuring chamber.

3. A measuring apparatus in accordance with claim 1, wherein the distance sensor unit includes at least one device for generation of an electrical and/or magnetic field and at least one sensor for measurement of the generated magnetic and/or electrical field or a change therein.

4. A measuring apparatus in accordance with claim 3, wherein the field generation device includes a least one permanent magnet for generation of a magnetic field and the field sensor includes a magneto-resistive sensor.

5. A measuring apparatus in accordance with claim 1, wherein the measuring element includes an ultrasonic transmitter and an ultrasonic receiver which are arranged with respect to the measuring chamber so as to allow an ultrasonic run time measurement to be taken through the measuring chamber.

6. A measuring apparatus in accordance with claim 1, wherein the apparatus is suitable for use in haemo-dialysis and for determination of blood parameters.

7. A measuring apparatus in accordance with claim 1, wherein the apparatus is suitable for determination of density and/or concentration and/or haemocrit value of the medical fluid.

8. A measuring apparatus in accordance with claim 1, wherein the distance sensor unit is arranged laterally offset with respect to said measuring chamber received in the measuring chamber device.

9. A measuring apparatus in accordance with claim 1, wherein at least two distance sensor units are arranged offset with respect to one another.

10. A method for the determination of a parameter of a medical fluid, comprising the steps of:
    leading the fluid through a measuring chamber;
    measuring a measured value whose value depends on an extent of the measuring chamber in a measuring direction, said measured value allowing for determination of the parameter, or of a value being in a fixed relationship thereto, with a known value for said extent of the measuring chamber; and
    said measurement of the measured value additionally determining a value that is in a fixed relationship with the extent of the measuring chamber in the measuring direction, or a change in said extent.

11. A method in accordance with claim 10, wherein the extent is determined using an electrical and/or magnetic field which is generated by a field generation device at a location of a field sensor, said field generation device and said field sensor being arranged such that a distance therebetween is in a fixed relationship with the extent.

12. A method in accordance with claim 11, wherein a magnetic field is generated by said field generation device having at least a permanent magnet, said field sensor including a magneto-resistive sensor for measuring a strength and/or direction of said magnet.

13. A method in accordance with claim 10, wherein the change in the extent is determined from a change in an electrical and/or magnetic field which results from a change in a distance between a field generation device and a field sensor.

14. A method in accordance with claim 10, wherein the measured value includes a run time of an ultrasonic wave.

15. A method in accordance with claim 10, wherein the medical fluid includes blood and the method is used in haemo-dialysis.

16. A method in accordance with claim 10 wherein the parameter to be determined is density and/or concentration and/or haemocrit value.

17. A method for the calibration of a measuring apparatus having a measuring chamber through which a medical fluid to be measured is guided, at least one measuring element for measuring a measured value whose value depends on an extent of the measuring chamber, and at least one distance sensor unit, comprising the steps of:
    a) sending a fluid with a known value of a parameter through the measuring chamber, with the measuring apparatus being suitable for determination of said parameter;
    b) determining a measured value by the measuring element whose value depends on the extent of the measuring chamber in a measuring direction;
    c) determining the extent of the measuring chamber in the measuring direction from the known parameter value and the measured value or from a value that is in a fixed relationship thereto;
    d) measuring a signal of the distance sensor unit;
    e) associating the measured signal with the determined value of the extent of the measuring chamber or with the value that is in a fixed relationship thereto;
    f) changing the extent of the measuring chamber; and g) repeating the steps b) to f) at least once for determination of a characteristic curve between the signal of the distance sensor unit and the extent of the measuring chamber, or the value that is in a fixed relationship thereto.

18. A method for the calibration in accordance with claim 17, wherein the parameter is ultrasound velocity, the measuring element includes an ultrasonic transmitter and an ultrasonic receiver and the measured value is an ultrasonic run time.

19. A method for the calibration in accordance with claim 18, wherein saline solution is used as the fluid for calibration.

* * * * *

UNITED STATES PATENT AND TRADEMARK OFFICE
CERTIFICATE OF CORRECTION

PATENT NO. : 6,821,432 B2
DATED : November 23, 2004
INVENTOR(S) : Klaus Metzner

It is certified that error appears in the above-identified patent and that said Letters Patent is hereby corrected as shown below:

Title page,
Item [57], ABSTRACT,
Line 2, change "including" to -- includes --;
Line 8, change "the" (first occurrence) to -- for --; and Column 5,
Line 15, change "transmitter" to -- transmitters --

Signed and Sealed this

Seventeenth Day of May, 2005

JON W. DUDAS
*Director of the United States Patent and Trademark Office*